(12) United States Patent
Crepel et al.

(10) Patent No.: US 9,257,723 B2
(45) Date of Patent: Feb. 9, 2016

(54) ARYL DIAZONIUM SALT AND USE IN AN ELECTROLYTIC SOLUTION OF AN ELECTROCHEMICAL GENERATOR

(75) Inventors: Laureline Crepel, Grenoble (FR); Fannie Alloin, Vizille (FR); Jean-Claude Lepretre, Voreppe (FR); Sebastien Martinet, Saint Quentin sur Isere (FR)

(73) Assignee: COMMISSARIAT À L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 174 days.

(21) Appl. No.: 13/824,052

(22) PCT Filed: Sep. 19, 2011

(86) PCT No.: PCT/FR2011/000508
§ 371 (c)(1),
(2), (4) Date: Mar. 15, 2013

(87) PCT Pub. No.: WO2012/035218
PCT Pub. Date: Mar. 22, 2012

(65) Prior Publication Data
US 2013/0189574 A1 Jul. 25, 2013

(30) Foreign Application Priority Data
Sep. 17, 2010 (FR) .................................. 10 03706

(51) Int. Cl.
*H01M 10/26* (2006.01)
*C07C 245/20* (2006.01)
*H01M 10/052* (2010.01)
*H01M 10/0568* (2010.01)
*H01G 11/62* (2013.01)

(52) U.S. Cl.
CPC ............. *H01M 10/26* (2013.01); *C07C 245/20* (2013.01); *H01G 11/62* (2013.01); *H01M 10/052* (2013.01); *H01M 10/0568* (2013.01); *Y02E 60/122* (2013.01); *Y02E 60/13* (2013.01)

(58) Field of Classification Search
CPC .................................................... H01M 10/26
USPC .......................................... 429/207, 212, 337
See application file for complete search history.

(56) References Cited

U.S. PATENT DOCUMENTS 3,778,270 A * 12/1973 Roos .............................. 430/162
4,670,175 A * 6/1987 Shinozaki et al. ........... 252/62.2

2007/0289872 A1 * 12/2007 Deniau et al. ................. 205/157
2009/0155696 A1 * 6/2009 Lee et al. ....................... 429/337
2010/0028745 A1 2/2010 Salguero et al.

FOREIGN PATENT DOCUMENTS

| JP | A-11-352679 | 12/1999 |
| JP | A-2000-77073 | 3/2000 |
| JP | A-2000-340256 | 12/2000 |
| WO | WO 02/060812 A2 | 8/2002 |

OTHER PUBLICATIONS

Journal of Inclusion Phenomena and Motecular Recognition in Chemistry 16 383-402, 1993.*
J. Med. Chem. 2004, 47, 1709-1718.*
p-Nitrobenzyl Bromide e-EROS Encyclopedia of Reagents for Organic Synthesis, 2001.*
Brooksby et al., "Electrochemical and Atomic Force Microscopy Study of Carbon Surfaces Modification via Diazonium Reduction in Aqueous and Acetonitrile Solutions," *Langmuir*, 2004, vol. 20, pp. 5038-5045.
Tanguy et al., "Lowering Interfacial Chemical Reactivity of Oxide Materials for Lithium Batteries. A Molecular Grafting Approach," *Journal of Materials Chemistry*, 2009, vol. 19, pp. 4771-4777.
Lahiri et al., "Solvophobically Driven π-Stacking of Phenylene Ethynylene macrocycles and Oligomers," *J. Am. Chem. Soc.*, 2000, vol. 122, pp. 11315-11319.
Lahiri, "Syntheses of Oligomers," *J. Am. Chem. Soc.*, 2000, Supporting Information pp. 1-39.

* cited by examiner

*Primary Examiner* — Patrick Ryan
*Assistant Examiner* — Alex Usyatinsky
(74) *Attorney, Agent, or Firm* — Oliff PLC (57) ABSTRACT

The invention relates to a diazonium aryl salt devoid of hydroxyl functions of the following general formula (1):

$$X^{-+}N\equiv N\text{-}A\text{-}R_1\text{---}(OR_2)_n\text{---}O\text{---}R_4\text{-}A'\text{-}N\equiv N^+X^- \quad (1)$$

in which: n is in a range of from 1 to 10, preferably from 1 to 4, $X^-$ represents a counter-ion of the diazonium cation selected from the group consisting of halogenides, $BF_4-$, $NO_3-$, $HSO_4-$, $PF_6-$, $CH_3COO-$, $N(SO_2CF_3)_2-$, $CF_3SO_3-$, $CH_3SO_3-$, $CF_3COO-$, $(CH_3O)(H)PO_2-$, and $N(CN)_2-$;

$R_1$, $R_2$ and $R_4$ are identical or different and are independently selected from the group consisting of —$CH_2$—, a cyclic alkyl group, an acyclic alkyl group, a linear alkyl group, and a branched alkyl group; and A and A' are identical or different and independently represent a mono or polycyclic, aromatic hydrocarbonated group chosen from the group formed by phenyl, aryl groups, condensed polyaromatic groups, which may be substituted.

18 Claims, 3 Drawing Sheets

ARYL DIAZONIUM SALT AND USE IN AN ELECTROLYTIC SOLUTION OF AN ELECTROCHEMICAL GENERATOR

BACKGROUND OF THE INVENTION

The invention relates to a diazonium salt and the use of the latter in an electrolytic solution of an electrochemical generator.

STATE OF THE ART

Electrolytes used for electrochemical generators are conventionally formed by a solvent and an electrolytic salt. The notion of electrochemical generators refers to both storage batteries and to super-capacitors. A storage battery is defined as an energy storage system using electrochemical reactions in order to store and restore electric power. Li-ion batteries generally use organic solvent-based electrolytes containing a dissolved lithium salt. A super-capacitor is an electrochemical capacitor enabling a quantity of energy to be stored via adsorption reactions at the surface of the electrode materials and a power density to be restored, intermediate between batteries and conventional electrolytic capacitors.

Electrochemical generators, in particular Lithium-ion storage batteries, using aqueous electrolytes are however beginning to be developed.

An aqueous electrochemical storage battery is conventionally composed of a positive electrode and a negative electrode, a porous separator performing electronic insulation between the positive and negative electrodes, and a water-based electrolyte in which one or more salts performing ionic conductivity are dissolved. The commonly used salts are for example $H_2SO_4$ for lead storage batteries, a KOH—LiOH—NaOH mixture for alkaline storage batteries and a lithium salt such as $LiNO_3$, $Li_2SO_4$, LiOH for aqueous lithium storage batteries. The electrolyte impregnates all or part of the porosity of the electrodes and of the separator. Both the positive and negative electrodes are composed of a respectively positive and negative active material, an electronic conductor such as carbon black and carbon fibres, a thickener and a binder.

An aqueous super-capacitor is conventionally composed of two porous electrodes, integrating either compounds of active carbon type with a large specific surface, or transition metal oxides of $MnO_2$, $RuO_2$, $Li_4Ti_5O_{12}$, $TiO_2$ type, a porous separating membrane between the two electrodes, and an aqueous electrolyte in which one or more salts performing ionic conductivity such as KOH, $H_2SO_4$, $KNO_3$, $LiNO_3$, $NaSO_4$ are dissolved.

The performances of electrochemical generators can be affected by instability phenomena of the liquid organic or aqueous electrolyte when operation of the battery takes place. The electrolyte does in fact have to withstand the operating voltage of the battery which is comprised between 1.9V and 5V depending on the pair of electrodes used for the organic electrolytes and between 1.2V and 2V for aqueous electrolytes. For electrode potentials higher or lower than the stability of the electrolyte, catalysed parasite reactions of decomposition of the electrolyte at the surface of the electrodes are observed.

The development of solutions tending to eliminate or reduce this decomposition phenomenon is particularly crucial, in particular for aqueous electrolyte Lithium-Ion storage batteries for which this phenomenon is particularly constraining.

Figure 1:
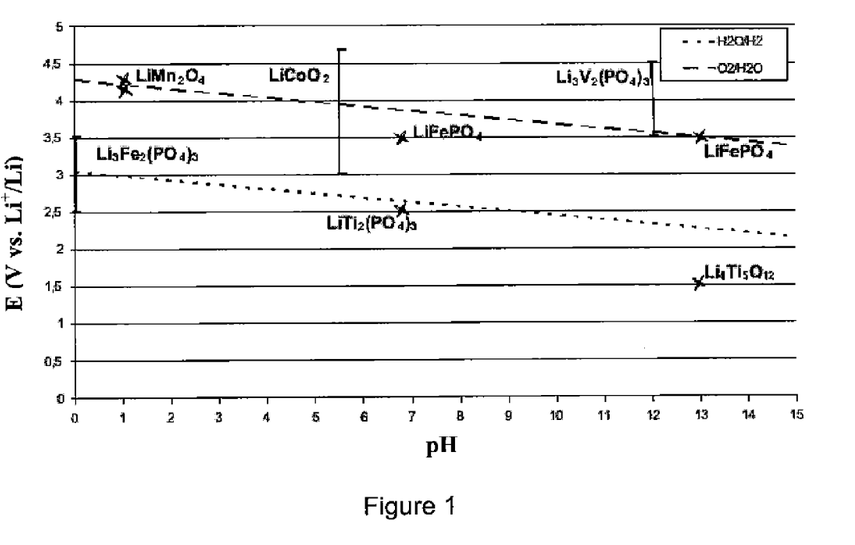
FIG. 1 corresponds to a stability diagram of water representing the nominal voltage of the water versus the pH as well as the insertion and extraction potentials of different active materials of a Lithium-Ion storage battery electrode.

As represented in FIG. 1, the thermodynamic stability window of water versus the pH is 1.23V and notably limits the choice of active materials for such an electrochemical generator. Thus, for the active materials of a Lithium-Ion storage battery having a lithium insertion and extraction potential situated outside the stability window of water, electrochemical decomposition of the water is observed. In the absence of overvoltage phenomenon, oxidation of water on the positive electrode is observed for potentials situated above the line represented by a dashed line (at the top in FIG. 1) and reduction of water on the negative electrode is observed for potentials situated below the line represented by a dotted line (at the bottom in FIG. 1). The overvoltage phenomena linked to oxidation and reduction of water are weak on lithium insertion materials. Decomposition of water is therefore observed for potentials close to those fixed by thermodynamics.

Solving this problem would make electrochemical generators with aqueous electrolyte attractive. In particular, this problem constitutes a technological hang-up for development of Lithium-Ion storage batteries with aqueous electrolyte. Overcoming this technological hang-up presents a great interest for Lithium-Ion storage batteries with an aqueous electrolyte, in particular from an economic, safety and performance standpoint, comparatively with Lithium-Ion storage batteries with an organic electrolyte which, in spite of a better nominal voltage, generate higher production and raw material costs and present mediocre high-power performances.

Different ways have been proposed to prevent or reduce the liquid electrolyte decomposition phenomenon. Patents JP-A-2000340256 and JP-A-2000077073 for example use the overvoltages at the electrodes to control the interfacial reactions.

Another proposed solution consists in passivating at least one electrode of the Lithium-ion storage battery in order to inhibit degradation of the liquid electrolyte. The document US-A-20090155696 proposes providing an insulating film on the electrode, by polymerization of a monomer present in the electrolyte of the storage battery.

Another method consists in forming a protective layer at the surface of an electrode by grafting via an electrochemical process of the aromatic group of an aryl diazonium salt thereby enabling the physical-chemical properties of the electrode material to be modified or improved.

Formation of an organic layer at the surface of a metallic, carbonated or insertion material by electrochemical reduction of a diazonium salt has been extensively described in the literature. This grafting mechanism has in particular been used to improve the corrosion resistance or to modify the interfacial reactivity of electrodes.

The general mechanism of grafting by electrochemical reduction is represented by the following reaction:

in which:

R is a substituent of the aryl group, X an anion such as a halogenide or a $BF_4^-$ ion, C is carbon, SC a semiconductor and M a metal.

For example, Brooksby, P. A. et al. described in the article "Electrochemical and Atomic Force Microscopy Study of Carbon Surface Modification via Diazonium Reduction in Aqueous and Acetonitrile Solutions", (Langmuir, 2004, 20, P.

5038-5045), a study concerning electrochemical reduction of 4-nitrobenzene-diazonium and 4-nitroazobenzene-4'-diazonium salts in an acid and acetonitrile medium, at the surface of a substrate covered by a photosensitive resin. The authors highlighted the creation of a covalent carbon-carbon (substrate/organic product) bond and the influence of several parameters such as the duration of the electrochemical reduction step, the applied potential, the type of substrate, the concentration of diazonium salts and the chemical groups conveyed by this salt on the thickness and structure of the film formed in this way.

Recently, works by Tanguy, F. et al. have proposed to fabricate a passivation layer on positive electrodes of an oxide-based Lithium-ion battery by grafting of a diazonium aryl salt. In the article "Lowering interfacial chemical reactivity of oxide materials for lithium batteries. A molecular grafting approach", (Journal of Materials Chemistry, 2009, no. 19, P. 4771-4777), Tanguy, F. showed that 4-nitro-benzenediazonium-tetrafluoroborate salt $(NO_2C_6H_4N_2{}^+BF_4{}^-)$ dissolved in an organic ethylcarbonate-dimethylcarbonate (EC-DMC—LiF$_6$) electrolyte forms an organic layer at the surface of a Li$_{1.1}$V$_3$O$_8$ electrode by chimiosorption. Grafting by electrochemical reduction of the diazonium salt at the surface of the Li$_{1.1}$V$_3$O$_8$ positive electrode takes place when a lower potential than the reduction potential of the diazonium salt is imposed on the electrode. The presence of an organic layer obtained by such a method does not limit the charge transfer of the electrode and greatly inhibits the catalysed decomposition of the organic electrolyte at the surface of the electrode.

OBJECT OF THE INVENTION

The object of the invention is to propose an alternative to known diazonium salt.

It is a further object of the invention to propose an improved electrolytic solution for an electrochemical generator, in particular remedying the shortcomings of the prior art.

In particular, the object of the invention is to propose an aqueous electrolytic solution for a Lithium-Ion storage battery that is stable up to a high operating voltage and having a broader stability window versus the pH than that of the aqueous electrolytic solutions of a Lithium-Ion storage battery of the prior art.

According to the invention, this object is achieved by a diazonium salt and the use of such a salt according to the appended claims.

BRIEF DESCRIPTION OF THE DRAWINGS

Other advantages and features will become more clearly apparent from the following description of particular embodiments of the invention given for non-restrictive example purposes only and represented in the appended drawings, in which.

DESCRIPTION OF PARTICULAR EMBODIMENTS

A family of diazonium salts is proposed that is particularly advantageous for use in an initial electrolytic solution of an electrochemical generator, i.e. of a super-capacitor or a storage battery.

What is meant by "initial" electrolytic solution of an electrochemical generator is an electrolytic solution present in the electrochemical generator before the first charging of this generator. Initial electrolytic solutions containing such salts are more stable than those of the prior art and participate in improving the performances of the generator, in particular of a Lithium-Ion storage battery.

The improvement is particularly significant in the case of use in an aqueous electrolytic solution. It has in fact been surprisingly observed that this family of diazonium salts notably slows down the oxidation and reduction kinetics of water on the electrodes of the electrochemical generator without however affecting the performances of the electrochemical generator, and in particular without limiting the charge transfer kinetics associated with insertion/extraction of the lithium cation in the intercalation material of a Lithium-Ion storage battery.

According to a particular embodiment, the diazonium salt has the following general formula (1):

$$X^-{}^+N\!\equiv\!N\text{-}A\text{-}R_1\text{—}(OR_2)_n\text{—}OR_3 \qquad (1)$$

in which n is an integer comprised between 1 and 10, preferably between 1 and 4, X$^-$ represents a counter-ion of the diazonium cation chosen from the halogenides, BF$_4{}^-$, NO$_3{}^-$, HSO$_4{}^-$, PF$_6{}^-$, CH$_3$COO$^-$, N(SO$_2$CF$_3$)$_2{}^-$, CF$_3$SO$_3{}^-$, CH$_3$SO$_3$, CF$_3$COO$^-$, (CH$_3$O)(H)PO$_2{}^-$, N(CN)$_2{}^-$, R$_1$ is chosen from the group formed by —CH$_2$—, a cyclic or acyclic, linear or branched alkyl chain preferably comprising from 1 to 6 carbon atoms, R$_2$ is chosen from the group formed by —CH$_2$—, a cyclic or acyclic, linear or branched alkyl chain preferably comprising from 2 to 6 carbon atoms, preferably a methylene-, ethylene-, n-propylene-, iso-propylene-, n-butylene-, tert-butylene-, sec-butylene- and n-pentylene-group, R$_3$ is chosen from the group formed by —CH$_3$, a cyclic or acyclic, linear or branched alkyl chain preferably comprising from 2 to 6 carbon atoms and a group of the following formula (2):

(2)

in which

A' is a mono or polycyclic, aromatic hydrocarbonated group chosen from the group formed by phenyl, aryl groups, and condensed polyaromatic groups, which may be substituted, $R_4$ is chosen from the group formed by —$CH_2$—, a cyclic or acyclic, linear or branched alkyl chain preferably comprising from 2 to 8 carbon atoms, and A is identical to or different from N and represents a mono- or polycyclic, aromatic hydrocarbonated group chosen from the group formed by phenyl, aryl groups, and condensed polyaromatic groups, which may be substituted, with the exception of the group of formula (3), represented below, when $R_3$ is chosen from the group formed by —$CH_3$, a cyclic or acyclic, linear or branched alkyl chain:

(3)

in which $R_5$ and $R_6$ are identical or different and chosen independently from the group formed by —$CH_3$, a cyclic or acyclic, linear or branched alkyl group.

What is meant by aryl group is an aromatic system having one or more aromatic cycles, which may be substituted.

When A and/or A' is an aryl group, an aryl group comprising from 6 to 9 carbon atoms will be preferably chosen, for example a phenyl, tolyl, xylyl, trimethyl-phenyl group. In all cases, the diazonium function is carried on the aromatic cycle of the aryl group.

What is meant by condensed polyaromatic group is a polycyclic aromatic system formed by several fusioned benzene rings. The diazonium function can be carried on any one of the aromatic cycles of the condensed polyaromatic group.

When A and/or A' is a condensed polyaromatic group, a polyaromatic group will preferably be chosen comprising from 10 to 45 carbon atoms, possibly substituted by one or more groups chosen from the group formed by —H, —CH3, a halogenide, a linear or branched alkyl chain, comprising from 2 to 8 carbon atoms, and possibly one or more heteroatoms chosen from O, S and N.

The diazonium salt is devoid of hydroxyl functions so as to minimize the affinity of the diazonium salt with the water of the electrolytic solution, for example by preventing creation of bonds of Van der Waals and/or hydrogen type. In particular, $R_1$, $R_2$ and $R_3$ are advantageously devoid of hydroxyl functions in order to obtain a diazonium salt having an apolar part A and A' containing the aromatic hydrocarbonated group and an aprotic polar part constituted by a polyether chain.

A and A' can moreover be identical or different and be chosen from the phenyl, anthracenyle and naphtalenyle groups, which may be substituted, preferably by one or more groups chosen from the group formed by —H, —$CH_3$, a halogenide, a linear or branched alkyl chain comprising from 2 to 8 carbon atoms, and possibly one or more heteroatoms chosen from O, S and N.

According to a particular embodiment, the diazonium salt can advantageously be a bis-diazonium salt of formula (1) in which $R_3$ is a group of formula (2).

The diazonium salt can for example be a bis-diazonium salt of the following general formula (4):

(4)

in which:

n is an integer comprised between 1 and 10, preferably between 1 and 4, m is equal to 0 or 1, p is an integer comprised between 1 and 5, advantageously equal to 2, $X^-$ and $Y^-$ are identical or different and independently represent a counter-ion of the diazonium cation chosen from the halogenides, $BF_4^-$, $NO_3^-$, $HSO_4^-$, $PF_6^-$, $CH_3COO^-$, $N(SO_2CF_3)_2^-$, $CF_3SO_3^-$, $CH_3SO_3^-$, $CF_3COO^-$, $(CH_3O)(H)PO_2^-$, $N(CN)_2^-$,

$R_1$ and $R_4$ are identical or different and chosen independently from the group formed by a cyclic or acyclic, linear or branched alkyl chain preferably comprising from 1 to 6 carbon atoms, $R_7$ and $R_8$ are identical or different and chosen independently from the group formed by —H, —$CH_3$, a halogenide, a linear or branched alkyl chain preferably comprising from 2 to 8 carbon atoms, possibly containing one or more heteroatoms, advantageously chosen from O, S and N.

The bis-diazonium salt advantageously possesses a polyether chain enabling the cations, in particular the $Li^+$ ions, to be solvated. The polyether chain is advantageously a poly(oxyethylene). Thus, in formula (4) described above, m is preferably equal to 0 and p is comprised between 2 and 4, advantageously equal to 2.

Likewise, the polyether chain situated between the aromatic groups of A and A' is preferably in benzylic position. To achieve this, each of $R_1$ and $R_4$ advantageously represents a —$CH_2$— group, respectively in formulas (1) and (2).

According to another particular embodiment, the polyether chain is advantageously in para-position with respect to the diazonium functions. The diazonium salt has the following general formula (5):

(5)

in which:

n is an integer comprised between 1 and 10, preferably between 1 and 4, m is equal to 0 or 1, p is an integer comprised between 1 and 5, advantageously equal to 2,

X⁻ and Y⁻ are identical or different and independently represent a counter-ion of the diazonium cation chosen from the halogenides, BF₄⁻, NO₃⁻, HSO₄⁻, PF₆⁻, CH₃COO⁻, NSO₂CF₃)₂⁻, CF₃SO₃⁻, CH₃SO₃⁻, CF₃COO⁻, (CH₃O)(H)PO₂⁻, N(CN)₂⁻, R₁ and R₄ are identical or different and chosen independently from the group formed by —CH₂—, a cyclic or acyclic, linear or branched alkyl chain preferably comprising from 1 to 6 carbon atoms, R₇ and R₈ are identical or different and chosen independently from the group formed by —H, —CH₃, a halogenide, a linear or branched alkyl chain preferably comprising from 2 to 8 carbon atoms, possibly containing one or more heteroatoms, advantageously chosen from O, S and N.

R₇ and R₈ are chosen in such a way as to enhance the stability of the diazonium functions. Substituting the aromatic cycles with R₇ and R₈, methoxy or ethoxy groups, in ortho- and/or meta position with respect to the diazonium functions will for example be avoided. In formula (5), R₇ and R₈ can advantageously be identical and preferably represent a hydrogen atom.

A bis-diazonium salt of formula (5) can be obtained by a synthesis method comprising three steps. A first step consists in adding a polyether via one or two hydroxyl functions on nitro-bromomethyl-benzene, preferably 4-nitro-1-bromomethyl-benzene, according to the following reaction scheme (1):

The reaction step (1) enables the benzylic group of the 4-nitro-1-bromomethyl-benzene to be added at each end of a dihydroxylated polyether by means of the two free hydroxyl functions of the polyether chain. A polyether chain having a nitrobenzene group at each of its ends is thus obtained. By choosing different initial dihydroxylated polyethers, i.e. by choosing the value of n, m and p in appropriate manner, the length and nature of the polyether chain separating the two apolar aromatic cycles situated at the ends of the polyether formed in this way can easily be varied. What is meant by "nature" is the hydrophilic/hydrophobic character of the polyether chain and its solvatant character with respect to Lithium.

A second step consists in reducing the nitro group of the aromatic cycles of the obtained polyether into an amino group, by means of any known method, on completion of the first step. This step can for example be achieved by a conventional reduction using hydrazine, catalysed by carbonated palladium, noted Pd—C.

The compound of the following general formula (6) is then obtained:

A third step consists in a diazotization reaction by means of any known method, which enables the two amino groups to be transformed into diazonium groups. The diazotization reaction is achieved for example by addition of tetrafluoroboric acid and isoamyl nitrite to the diamine polyether obtained in the second step described in the foregoing. A bis-diazonium salt of general formula (5) is then obtained in which X⁻ represents the tetrafluoroborate counter-ion BF₄⁻.

Example I

In the synthesis method of a bis-diazonium salt, the bis(4-diazoniumbenzyl)-trioxyethylene tetrafluoroborate salt, noted DS3, was achieved from the 4-nitro-1-bromomethyl-benzene and the triethylene glycol according to the protocol described below. This salt corresponds to the bis-diazonium salt of formula (5) in which n=3, p=2, m=0 and X⁻ and Y⁻ are identical and represent the BF₄⁻ icon.

Step 1: Synthesis of the Nitrated Derivative

All the products are previously dried either on a molecular sieve for the triethylene glycol or in temperature in a vacuum for the silver oxide Ag₂O and the 4-nitro-1-bromomethyl-benzene. 10.39 g of 4-nitro-1-bromomethyl-benzene (i.e. 0.0481 mol) and 3.61 g of triethylene glycol (0.024 mol) are mixed in a round-bottom flask in 170 mL of dry dichloromethane (CH₂Cl₂), freshly distilled on calcium hydride. 22.2 g of Ag₂O oxide are added in excess (0.096 mol). The flask is maintained under argon for 48 hours under reflux in the CH₂Cl₂. Dry molecular sieve (dried in a vacuum at 300° C.) is added to the reaction medium to trap the water which forms when the reaction takes place.

The excess Ag₂O oxide and the silver bromide AgBr produced are eliminated by filtration or centrifugation in dichloromethane where the nitrated compound is soluble. After purification on a silica column with a dichloromethane/methanol mixture, 7.5 g (0.0178 mol) of pure and dry bis(4-nitrobenzyl)-trioxyethylene is obtained with a yield of 74%.

Step 2: Reduction of the Nitrated Derivative 5 mmol of previously obtained bis(4-nitrobenzyl)-trioxyethylene are mixed in a flask with 10 mL of monohydrated hydrazine, 80 mL of freshly distilled ethanol and 0.05 g of carbonated palladium (Pd—C) at 10%. This mixture is subjected to reflux during 24 hours by stirring and then filtered to remove the Pd—C. The filtrate obtained is then concentrated by a rotary evaporator in order to reduce its volume to a few tens of milliliters. The filtrate, once concentrated, is purified by successive extractions in a separating funnel by a mixture of dichloromethane/water so as to remove any traces of hydrazine. After drying in a vacuum, purified bis(4-aminobenzyl)-trioxyethylene is obtained with a yield of 80%, in the form of a pale yellow-coloured liquid.

Step 3: Diazotization 72.9 mmol of previously obtained bis(4-aminobenzyl)-trioxyethyleric are mixed in an Erlenmeyer flask with 364 mL of distilled ethanol. 438 mmol of tetrafluoroboric acid are added. The mixture is cooled to 0° C. by means of an ice bath. 438 mmol of isoamyl nitrite are then added drop by drop under magnetic stirring. The mixture is maintained at 0° C., under stirring, for 1 hour, an oil then being obtained. Diethylic ether is added in order to precipitate the bis(4-diazoniumbenzyl)-trioxyethylene tetrafluoroborate salt. Then the mixture is maintained at 0° C., under magnetic stirring, for about 1 hour. The mixture is then placed in the refrigerator overnight in order to complete precipitation. After filtration, bis(4-diazoniumbenzyl)-trioxyethylene tetrafluoroborate salt with a yield of 70% is obtained.

Figure 2:
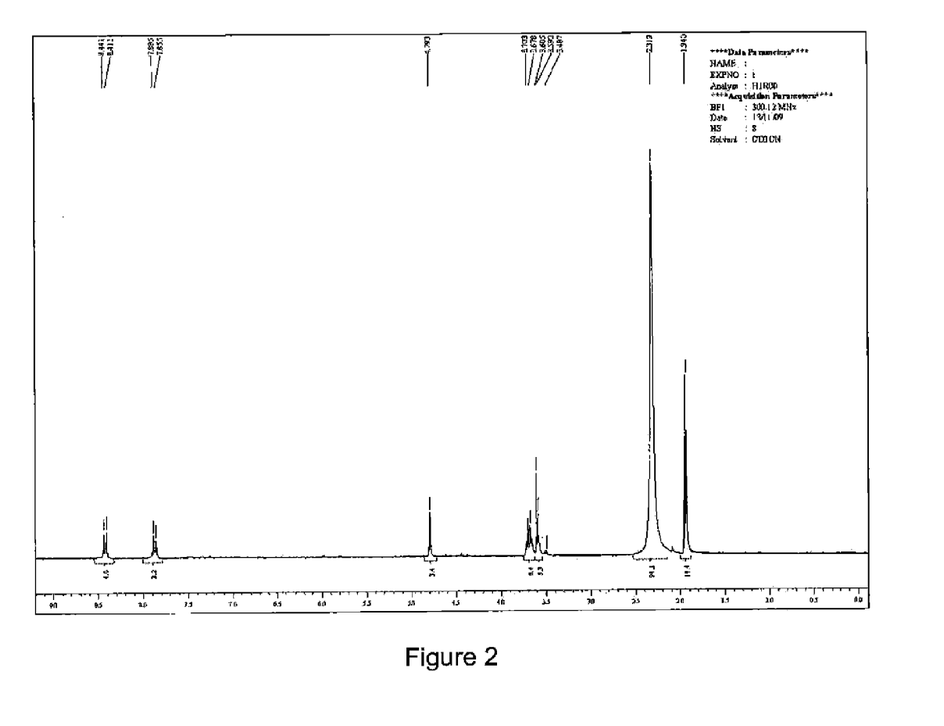
FIG. 2 represents a NMR $^1$H (300 12 MHz) spectrum of a diazonium salt according to the invention in acetonitrile ($d_H$=1.94 ppm), achieved with a Bruker Avance 300 spectrometer with a QNP 5 mm probe.

As represented in FIG. 2, the bis(4-diazoniumbenzyl)-trioxyethylene tetrafluoroborate salt is almost pure. Any traces of impurities can if required be eliminated by additional successive purification operations performed according to common practice in the field of chemical synthesis.

Several bis-diazonium salts were synthesized by means of the same operating mode varying the value n in formula (5) of the diazonium salt.

A diazonium salt, noted DS5, was also synthesized. DS5 has a structure of formula (1) with A being a phenyl group, $R_1$ a —$CH_2$— group, $R_2$ a —$CH_2$—$CH_2$— group, $R_3$ a —$CH_3$ group and n=1.

The results are set out in table I below:

TABLE I

| Reference/ value of n:m:p in formula (1) | Diazonium molecule | Initial polyether | Global yield % |
|---|---|---|---|
| DS2/ 2:0:2 | | HO–CH₂CH₂–O–CH₂CH₂–OH | 20 |
| DS3/ 3:0:2 | | HO–CH₂CH₂–O–CH₂CH₂–O–CH₂CH₂–OH | 40 |
| DS4/ 4:0:2 | | HO–(CH₂CH₂O)₄–H | 40 |
| DS5/ 1:0:2 | | HO–CH₂CH₂–O–CH₃ | 30 |

TABLE I-continued

| Reference/ value of n:m:p in formula (1) | Diazonium molecule | Initial polyether | Global yield % |
|---|---|---|---|
| DS6/ 2:1:1 | (structure) | (structure) | 35 |
| DS7/ 3:1:1 | (structure) | (structure) | 30 |

Although the particular embodiments described in the foregoing describe a diazonium salt the diazonium function of which is in para-position on the aromatic hydrocarbonated group of A, and of A' if applicable, the scope of the invention is not limited to this position. It can also be envisaged to produce a diazonium salt the diazonium function or functions of which are in ortho- or meta-position by means of a similar synthesis method to the method described in the foregoing, by choosing suitable initial products.

An electrolytic solution comprising the diazonium salt described above can advantageously be used in a non-charged Lithium-Ion storage battery so as to form a passivation layer on an electrode of the Lithium-Ion storage battery, when the first charge is performed.

According to a particular embodiment, an electrode of a Lithium-Ion storage battery is passivated by electrochemical reduction of an initial electrolytic solution containing the diazonium salt described above.

The Lithium-Ion storage battery comprises first and second electrodes insulated from one another by a separator. The separator can be a macroporous film made from Polyethylene or polypropylene, cellulose or polyvinylidene fluoride impregnated by an electrolytic solution.

The first electrode is preferably formed by a material chosen from metals and their alloys, carbon, semiconductors and lithium insertion materials.

The base of the first electrode constituting the negative electrode can for example be $Li_4Ti_5O_{12}$, $Li_3Fe_2(PO_4)_3$ or $TiO_2$, or a mixture of these materials, and may be supported by a copper strip. The base of the second electrode constituting the positive electrode can for example be $LiCoO_2$, $LiMn_2O_4$, $LiFePO_4$, $Li_3V_2(PO_4)_3$ or other lamellar oxides such as $LiNiCoAlO_2$ and its derivatives, and may be supported by an aluminium strip. The following positive and negative electrode pairs: $LiMn_2O_4/Li_3Fe_2(PO_4)_3$, $LiCoO_2/Li_4Ti_5O_{12}$, $LiCoO_2/LiTi_2(PO_4)_3$, $LiFePO_4/Li_4Ti_5O_{12}$, $Li_3V_2(PO_4)_3/Li_4Ti_5O_{12}$ can be cited for example purposes.

The first and second electrodes are separated by a final electrolytic solution. What is meant by "final" electrolytic solution is the electrolytic solution present in the Lithium-Ion storage battery after a first charging of the Lithium-Ion storage battery containing the initial electrolytic solution has been performed. The Lithium-Ion storage battery containing the initial electrolytic solution is non-charged, i.e. it has not been subjected to any charge.

The initial or final electrolytic solution is preferably an aqueous solution. The initial or final electrolytic solution advantageously comprises a salt the cation of which is at least partly the lithium $Li^+$ ion dissolved in a solvent or a mixture of solvents. The solvent is preferably an aqueous solvent. What is meant by aqueous solvent is a solvent containing water as its major constituent.

The salt advantageously has to withstand the operating voltage of the Lithium-Ion storage battery formed. The lithium salt can conventionally be lithium nitrate, $LiNO_3$.

The first electrode is covered by a passivation layer. The passivation layer is remarkable in that it comprises a compound formed by repetition of a pattern of the following formula (7):

(7)

in which n is an integer comprised between 1 and 10, preferably between 1 and 4, $R_1$ is chosen from the group formed by —$CH_2$—, a cyclic or acyclic, linear or branched alkyl chain preferably comprising from 1 to 6 carbon atoms, $R_2$ is chosen from the group formed by —$CH_2$—, a cyclic or acyclic, linear or branched alkyl chain preferably comprising from 2 to 6 carbon atoms, for example a methylene, ethylene-, n-propylene-, iso-propylene-, n-butylene-, tert-butylene-, sec-butylene- or n-pentylene-group, $R_3$ is chosen from the group formed by —$CH_3$, a cyclic or acyclic, linear or branched alkyl chain preferably comprising, preferably, from 2 to 6 carbon atoms and a group of the following formula (8):

(8)

in which

A' is a mono or polycyclic, aromatic hydrocarbonated group chosen from the group formed by phenyl, aryl groups, condensed polyaromatic groups, which may be substituted, $R_4$ is chosen from the group formed by —$CH_2$—, a cyclic or acyclic, linear or branched alkyl chain preferably comprising, preferably, from 2 to 8 carbon atoms and, A is identical to or different from A' and represents a mono or polycyclic, aromatic hydrocarbonated group chosen from the group formed by phenyl, aryl groups, condensed polyaromatic groups, which may be substituted.

When A and/or A' is an aryl group, an aryl group comprising from 6 to 9 carbon atoms will preferably be chosen, for example a phenyl, tolyl, xylyl, trimethyl-phenyl or tetramethyl-phenyl group.

When A and/or A' is a condensed polyaromatic group, a polyaromatic group will preferably be chosen comprising from 10 to 45 carbon atoms, which may be substituted by one or more groups chosen from the group formed by —H, —CH3, a halogenide, a linear or branched alkyl chain comprising from 2 to 8 carbon atoms, and possibly one or more heteroatoms chosen from O, S and N.

The pattern is devoid of hydroxyl functions to form a barrier against penetration of water and comprises at least one polyether chain favouring the interactions between the passivation film formed on the first electrode and the cation, preferably $Li^+$, present in the final electrolytic solution. In formulas 7, 8 and 9, it should be pointed out that the hatched part corresponds to the electrode surface.

The pattern is further grafted onto the first electrode by group A, and when $R_3$ is a group of formula (8), by the two groups A and A'.

The pattern is grafted onto the material of the first electrode by means of an aromatic hydro carbonated cycle of group A and, when $R_3$ is a group of formula (8), by an aromatic hydrocarbonated cycle of each of the groups A and A', the bond linking the first electrode and the pattern being a covalent bond of C-aromatic/metal or C— aromatic/carbon type.

The presence of a polyether chain has a large solvatant effect of the $Li^+$ lithium ions which enhances passage of the lithium ions through the passivation layer, to be inserted in the first electrode. The kinetics of the insertion and extraction reactions of the $Li^+$ ions in the material of the first electrode are consequently not significantly slowed down.

Furthermore, the apolar aromatic cycles of the patterns create a hydrophobic area in proximity to the surface of the first electrode. This hydrophobic area limits the approach of water, or can advantageously prevent water from reaching the first electrode. The water reduction reaction which in particular affects the performances of a Lithium-Ion storage battery with aqueous electrolyte is thus greatly limited or even totally eliminated, at the operating potential of the first electrode, due to the presence of this passivation layer.

Polyether chains able to solvate the cations of the final electrolytic solution, for example $Li^+$ ions, will consequently preferably be chosen. In particular, a polyether chain will be chosen having a suitable conformation and/or a sufficient ether function number so as to solvate the $Li^+$ ions and/or to create a selective circulation of the $Li^+$ ions through the passivation layer that is discriminant with respect to water.

According to a preferred particular embodiment, in formulas (7) and (8), $R_1$ and $R_4$ are identical and each of $R_1$ and $R_4$ can for example represent a —$CH_2$— group to obtain a polyether chain in benzylic position.

According to another preferred particular embodiment, the pattern can form a bridge structure at the surface of the first electrode. In formula (7), $R_3$ is advantageously a group of formula (8). The bridge structure at the surface of the first electrode enables the aprotic, polar polyether chain to be oriented towards the final electrolytic solution of the charged Lithium-Ion storage battery.

A and A' can be identical or different and chosen from the phenyl, anthracenyle and naphtalenyle groups, which may be substituted, preferably by one or more groups chosen from the group formed by —H, —$CH_3$, a halogenide, a linear or branched alkyl chain comprising from 2 to 8 carbon atoms, and possibly one or more heteroatoms chosen from O, S and N.

The pattern of the passivation layer can advantageously be represented by the following general formula (9):

in which:

n is an integer comprised between 1 and 10, preferably between 1 and 4, m is equal to 0 or 1, p is an integer comprised between 1 and 5, advantageously equal to 2, $R_1$ and $R_4$ are identical or different and chosen independently from the group formed by —$CH_2$—, a cyclic or acyclic, linear or branched alkyl chain preferably comprising from 1 to 6 carbon atoms, $R_7$ and $R_8$ are identical or different and chosen independently from the group formed by —H, —CH$_3$, a halogenide, a linear or branched alkyl chain preferably comprising from 2 to 8 carbon atoms, possibly containing one or more heteroatoms advantageously chosen from O, S and N.

In particular, the pattern of the passivation layer is represented by the following general formula (10):

(10)

in which:

n is an integer comprised between 1 and 10, preferably between 1 and 4, m is equal to 0 or 1, p is an integer comprised between 1 and 5, advantageously equal to 2, $R_1$ and $R_4$ are identical or different and chosen independently from the group formed by —CH$_2$—, a cyclic or acyclic, linear or branched alkyl chain preferably comprising from 1 to 6 carbon atoms, $R_7$ and $R_8$ are identical or different and chosen independently from the group formed by —H, —CH$_3$, a halogenide, a linear or branched alkyl chain preferably comprising from 2 to 8 carbon atoms, possibly containing one or more heteroatoms advantageously chosen from O, S and N.

$R_7$ and $R_8$ are preferably identical and represent a hydrogen atom, —H.

According to a particular embodiment, a method for producing a Lithium-Ion storage battery comprises a step of formation of an electrochemical cell, according to any known method, comprising the first and second electrodes separated by an initial electrolytic solution.

The initial electrolytic solution comprises a diazonium salt devoid of hydroxyl functions and of the following general formula (11):

$$X^{-+}N\equiv N\text{-}A\text{-}R_1(OR_2)_n\text{—}OR_3 \quad (11)$$

in which n is an integer comprised between 1 and 10, preferably between 1 and 4, $X^-$ represents a counter-ion of the diazonium cation chosen from the halogenides, $BF_4^-$, $NO_3^-$, $HSO_4^-$, $PF_6^-$, $CH_3COO^-$, $N(SO_2CF_3)_2^-$, $CF_3SO_3^-$, $CH_3SO_3^-$, $CF_3COO^-$, $(CH_3O)(H)PO_2^-$, $N(CN)_2^-$, $R_1$ and $R_2$ are identical or different and chosen independently from the group formed by —CH$_2$—, a cyclic or acyclic, linear or branched alkyl chain preferably comprising from 1 to 8 carbon atoms, $R_3$ is chosen from the group formed by —CH$_3$, a cyclic or acyclic, linear or branched alkyl chain preferably comprising from 2 to 8 carbon atoms, and a group of the following formula (12):

(12)

in which

A' is a mono or polycyclic, aromatic hydrocarbonated group chosen from the group formed by phenyl, aryl groups, condensed polyaromatic groups, which may be substituted, $R_4$ is chosen from the group formed by —CH$_2$—, a cyclic or acyclic, linear or branched alkyl chain preferably comprising from 2 to 8 carbon atoms and, A is identical to or different from A' and represents a mono or polycyclic, aromatic hydrocarbonated group chosen from the group formed by phenyl, aryl groups, condensed polyaromatic groups, which may be substituted.

When A and/or A' is an aryl group, an aryl group comprising from 6 to 9 carbon atoms will preferably be chosen, for example a phenyl, tolyl, xylyl, trimethyl-phenyl group.

When A and/or A' is a condensed polyaromatic group, a polyaromatic group will preferably be chosen comprising from 10 to 45 carbon atoms, possibly substituted by one or more groups chosen from the group formed by —H, —CH3, a halogenide, a linear or branched alkyl chain comprising from 2 to 8 carbon atoms, and possibly one or more heteroatoms chosen from O, S and N.

The first step of assembly of the electrochemical cell advantageously enables a non-charged Lithium-Ion storage battery, forming the electrochemical cell, to be produced.

The first electrode is preferably the negative electrode where the water reduction reaction takes place.

The step of assembly of the electrochemical cell is followed by a formation step of the passivation layer on the first electrode of the electrochemical cell, by electrochemical reduction of the initial electrolytic solution.

The groups A and A' are preferably chosen for their stability properties, in particular electrochemical, at the reduction potential of the diazonium salt. The groups A and A' do not for example contain nitro, amine or ester functions in their structure. Likewise, the aromatic hydrocarbonated cycle or cycles of A and A' are advantageously not substituted, to prevent problems of steric dimensions that may affect the grafting yield of the diazonium salt on the first electrode.

The electrochemical reduction step enables the passivation layer to be formed in situ on the first electrode when first charging of the Lithium-Ion storage battery cell is performed.

To do this, the non-charged Lithium-Ion storage battery, formed on completion of the first step of the method, is subjected to an operating voltage when the first charging of the Lithium-Ion storage battery is performed, according to any known method.

The first charging enables both insertion of the lithium in the material of the first electrode and reduction of the diazonium salt present in the initial electrolytic solution. The first charging performs grafting of at least one aromatic hydrocarbonated cycle of group A and/or A' of the diazonium salt of formula (11) on the first electrode. The diazonium salt is consumed on first charging proportionally to the creation of the passivation layer on the first electrode.

The formation step of the passivation layer preferably comprises creation of a covalent bond of C-aryl/metal or C-aryl/carbon type between an aromatic hydrocarbonated cycle of group A and the material of the first electrode and an aromatic hydrocarbonated cycle of group A' and the material of the first electrode, when $R_3$ is a group of formula (8) in the pattern constituting the passivation layer.

After the first charge, the Lithium-Ion storage battery comprises the first electrode covered by the passivation layer described above and a final electrolytic solution separating the first and second electrodes.

On completion of the first charge, the whole of the diazonium salt has preferably been consumed, and the final electrolytic solution is then devoid of the diazonium salt.

The diazonium salt concentration in the initial electrolytic solution and the parameters of the first charge, in particular the duration and applied voltage, have an effect on the characteristics of the passivation layer, in particular on the thickness of the layer formed and the surface recovery rate.

The diazonium salt can advantageously be present in the initial electrolytic solution at a lower molar concentration than 0.5M, preferably comprised between 0.05M and 0.3M.

Example II

Passivation of a $LiFePO_4$ electrode passivated by electrochemical reduction of an aqueous initial electrolytic solution was performed by cyclic voltammetry. What is meant by "passivation" is the fact that the electrode is covered by a passivation layer as described in the foregoing.

The initial electrolytic solution is constituted by 10 mL of an aqueous solution of a $LiNO_3$ salt at a concentration of 5M and of a bis(4-diazoniumbenzyl)-trioxyethylene tetrafluoroborate salt, noted DS3, as synthesized in example 1, at a concentration of 2 mM.

The $LiFePO_4$ electrode is produced on a current collector according to any known Method. For example purposes, an ink is formed by a mixture of $LiFePO_4$ forming the insertion material, of carbon forming a conducting additive and of polymer binders forming a bonding agent. The ink is coated on a collector, for example made from nickel, and then dried to form the $LiFePO_4$ electrode. The $LiFePO_4$ electrode is then calandered and diced so as to be used in a conventional cyclic voltammetry assembly.

Cyclic voltammetry was achieved by means of a conventional assembly under argon with the initial electrolytic solution described above and three electrodes including the $LiFePO_4$ electrode as described above, noted $D_1$, constituting a working electrode, a saturated calomel electrode constituting the reference electrode, and a platinum wire for the counter-electrode.

Comparative measurements were also made on two other $LiFePO_4$ electrodes. The one noted $D_2$ is a $LiFePO_4$ electrode passivated according to the same operating protocol as before but with a 4-methoxybenzenediazonium tetrafluoroborate salt, noted $S_2$, marketed by Sigma-Aldrich, and the other electrode, noted $D_0$, is a bare $LiFePO_4$ electrode, i.e. devoid of a passivation layer, obtained by means of the same protocol but without addition of diazonium salt in the initial electrolytic solution.

Infrared (IR) spectra were performed on completion of the voltammetry on electrodes $D_1$ and $D_2$, to confirm formation of the passivation layer checking that the diazonium aryl salts DS3 and $S_2$ have been correctly grafted, respectively on $D_1$ and $D_2$.

Figure 3:
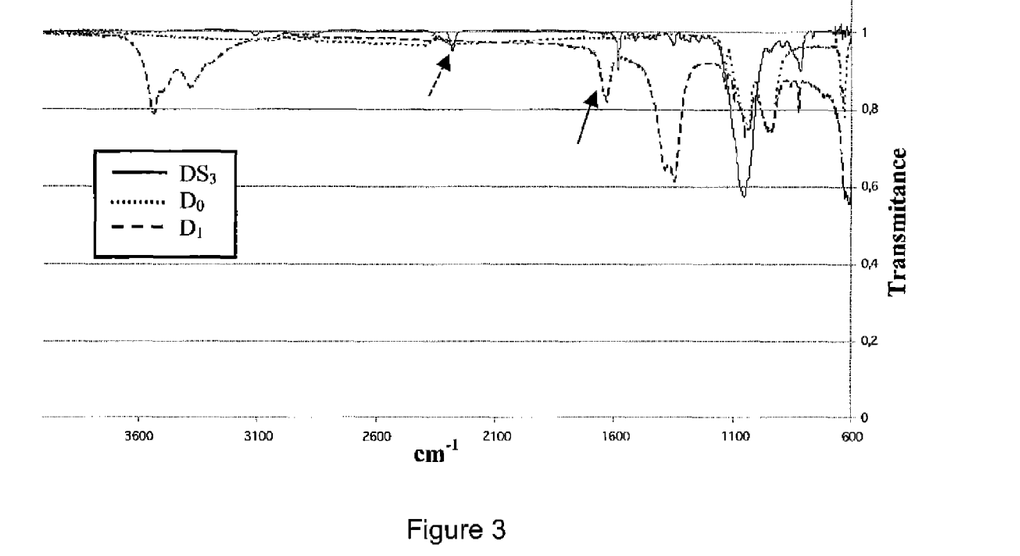
FIG. 3 represents the superposition of three spectra obtained according to an Attenuated Total Reflectance (ATR) method, of a sample of a diazonium salt according to the invention, noted DS$_3$, of a sample of a LiFePO$_4$ electrode, covered by a passivation layer according to the invention, noted D$_1$, and of a comparative sample of a bare LiFePO$_4$ electrode, noted D$_0$.

The IR spectra represented in FIG. 3 were obtained by an Attenuated Total Reflectance (abbreviated to ATR) method on the diazonium salt DS3 alone and on electrodes $D_0$ and $D_1$. Analysis of the $D_1$ spectrum comparatively with the DS3 and $D_0$ spectra effectively shows the disappearance of a peak situated in the region of 2200 $cm^{-1}$ characteristic of the diazonium function (broken-line arrow in FIG. 3) and the appearance of a peak around 1600 $\mu m^{-1}$ characteristic of an aromatic cycle substituted by an alkyl chain (continuous-line arrow in FIG. 3).

Figure 4:
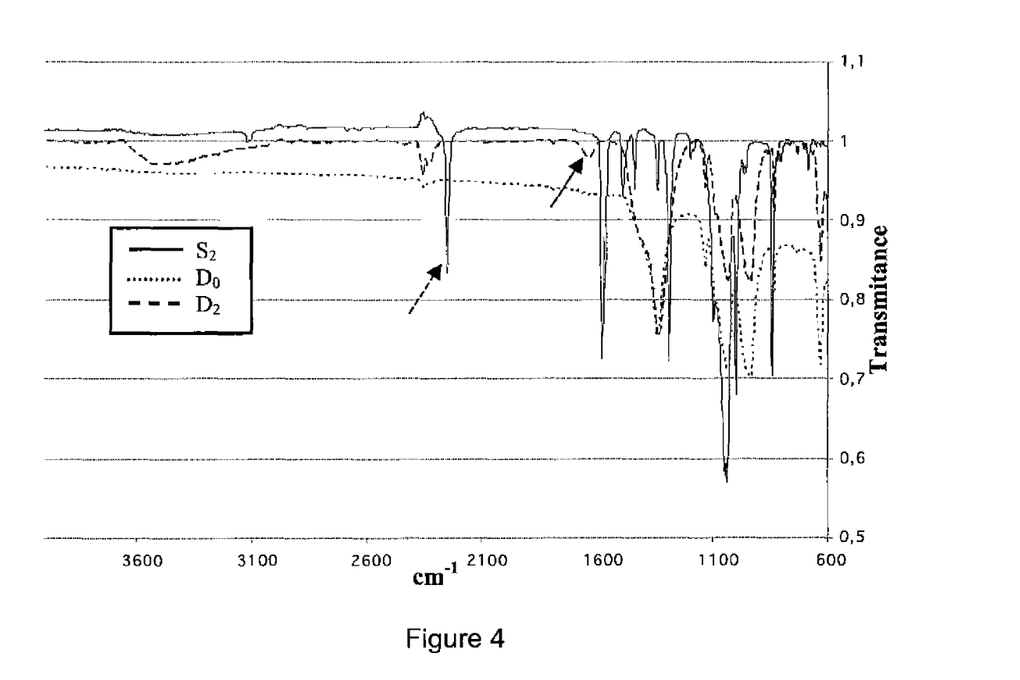
FIG. 4 represents the superposition of three infrared spectra obtained according to an ATR method, of a sample of a diazonium salt, noted S$_2$, and of two comparative samples, respectively of the bare electrode D$_0$ and of an electrode passivated with the S$_2$ salt, noted D$_2$.

The same observation can be made by analyzing the ATR spectra represented in FIG. 4 of the salt $S_2$ alone and of electrodes $D_0$ and $D_2$. Analysis of the spectrum of $D_2$ comparatively with the $S_2$ and $D_0$ spectra effectively shows the disappearance of the peak situated in the region of 2200 $cm^{-1}$ (broken-line arrow in FIG. 4) and the appearance of the peak around 1600 $cm^{-1}$ (continuous-line arrow in FIG. 4).

Figure 5:
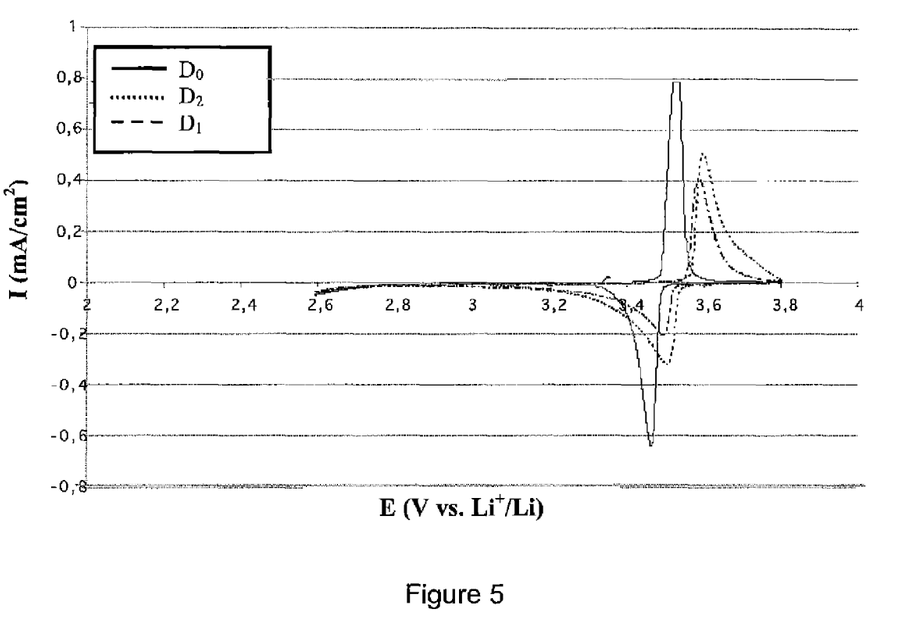
FIG. 5 represents three cyclic voltammetry plots obtained for an electrochemical cell respectively comprising the electrode D$_0$, D$_1$ and D$_2$ in a LiNO$_3$ 5M aqueous electrolyte.

The voltammetry measurements made with a scanning rate of 0.01 $mV \cdot s^{-1}$ on $D_0$, $D_1$ and $D_2$ are represented in FIG. 5. For the three electrodes $D_0$, $D_1$ and $D_2$, the curves obtained present symmetric lithium insertion and extraction peaks, characteristic of reversible systems. It can however be observed that the potential difference between the two insertion and extraction peaks is smaller for $D_1$ than for $D_2$. A potential difference of about 90 mV is in fact obtained for $D_1$, which is close to the value obtained for the bare electrode $D_0$, against 110 mV for $D_2$.

Other comparative measurements were also made on vitreous carbon electrodes in order to quantify the overvoltages obtained for each diazonium. Electrodes $C_1$, $C_2$, $C_3$, $C_4$, $C_5$ and $C_6$ were passivated according to the same operating protocol as for a $LiFePO_4$ electrode, respectively with S2, DS2, DS3, DS5, DS6 and DS7. The electrode C0 is the non-passivated electrode.

The current values obtained on the "one-way" scanning of the voltammetry for a potential of 1.8 V vs. $Li/Li^+$ and the overvoltage obtained, compared with the bare electrode, for a current density of $-0.05$ $mA/cm^2$ were measured with the different electrodes. The results are set out in the following table II:

TABLE II

| | Electrode reference | | | | | | |
|---|---|---|---|---|---|---|---|
| | $D_0$ | $C_1$ | $C_2$ | $C_3$ | $C_4$ | $C_5$ | $C_6$ |
| I (mA/$cm^2$) for E = 1.8 V | −2.90 | −0.33 | −0.38 | −0.68 | −0.54 | −0.54 | −0.54 |
| ΔE (mV) for I = −0.05 $mA/cm^2$ | 0 | 215 | 160 | 5 | 110 | 290 | 180 |

The comparative tests highlight the improvement of the electrochemical stability of the aqueous electrolyte according to the invention. Particularly interesting results obtained for C5 are also observed, with a high overvoltage of 290 mV and a weak current.

The aqueous electrolytic solution for an electrochemical generator, in particular for a Lithium-Ion storage battery, containing an aryl diazonium salt according to the invention is stable up to a high operating voltage. For electrochemical generators with an aqueous electrolyte, the presence of an aryl diazonium salt in the initial electrolytic solution enables the stability window of water to be broadened according to the pH, in particular by increasing the water reduction potential.

The invention claimed is:
1. An electrolytic solution comprising:
a diazonium salt devoid of hydroxyl functions, the diazonium salt having the following general formula:

in which:
n is an integer in a range of from 1 to 10,
X— represents a counter-ion of the diazonium cation selected from the group consisting of halogenides, $BF_4—$, $NO_3—$, $HSO_4—$, $PF_6—$, $CH_3COO—$, $N(SO_2CF_3)_2—$, $CF_3SO_3—$, $CH_3SO_3—$, $CF_3COO—$, $(CH_3O)(H)PO_2—$, and $N(CN)_2—$,
$R_1$, $R_2$ and $R_4$ are independently selected from the group consisting of $—CH_2—$, a cyclic alkyl group, an acyclic alkyl group, a linear alkyl group, and a branched alkyl group; and,
A and A' independently represent a mono or polycyclic, aromatic hydrocarbonated group chosen from the group formed by phenyl, aryl groups, condensed polyaromatic groups, which may be substituted.

2. The electrolytic solution according to claim 1, wherein n is in a range of from 1 to 4.

3. The electrolytic solution according to claim 1, wherein:
$R_1$ is independently selected from the group consisting of $—CH_2—$, a cyclic alkyl group, an acyclic alkyl group comprising from 1 to 6 carbon atoms, a linear alkyl group comprising from 1 to 6 carbon atoms, and a branched alkyl group comprising from 1 to 6 carbon atoms;
$R_2$ is independently selected from the group consisting of $—CH_2—$, a cyclic alkyl group, an acyclic alkyl group comprising from 2 to 6 carbon atoms, a linear alkyl group comprising from 2 to 6 carbon atoms, and a branched alkyl group comprising from 2 to 6 carbon atoms;
$R_4$ is independently selected from the group consisting of $—CH_2—$, a cyclic alkyl group, an acyclic alkyl group comprising from 2 to 8 carbon atoms, a linear alkyl group comprising from 2 to 8 carbon atoms, and a branched alkyl group comprising from 2 to 8 carbon atoms; and wherein
A and A' independently represent a mono or polycyclic, aromatic hydrocarbonated group chosen from the group formed by phenyl, aryl groups comprising from 6 to 10 carbon atoms, condensed polyaromatic groups comprising from 10 to 45 carbon atoms, which may be substituted by one or more groups selected from the group consisting of $—H$, $—CH_3$, a halogenide, a linear alkyl group comprising from 2 to 8 carbon atoms, and a branched alkyl group comprising from 2 to 8 carbon atoms.

4. The electrolytic solution according to claim 3, wherein A and A' independently represent a mono or polycyclic, aromatic hydrocarbonated group chosen from the group formed by phenyl, aryl groups comprising from 6 to 10 carbon atoms, condensed polyaromatic groups comprising from 10 to 45 carbon atoms, which may be substituted by one or more groups selected from the group consisting of
$—H$,
$—CH_3$,
a halogenide,
a linear alkyl group comprising from 2 to 8 carbon atoms and one or more heteroatoms chosen from O, S and N, and
a branched alkyl group comprising from 2 to 8 carbon atoms and one or more heteroatoms chosen from O, S and N.

5. The electrolytic solution according to claim 1, wherein $R_2$ is selected from the group consisting of methylene-, ethylene-, n-propylene-, iso-propylene-, n-butylene-, tert-butyl-, sec-butylene- and n-pentylene-.

6. The electrolytic solution according to claim 1, wherein each of $R_1$ and $R_4$ represents a $—CH_2—$ group.

7. The electrolytic solution according to claim 1, wherein A and A' are independently selected from the group consisting of phenyl, anthracenyle and naphtalenyle groups, which may be substituted.

8. The electrolytic solution according to claim 7, wherein A and A' are chosen independently from the phenyl, anthracenyle and naphtalenyle groups, which may be substituted by one or more groups selected from the group consisting of $—H$, $—CH_3$, a halogenide, a linear alkyl group comprising from 2 to 8 carbon atoms, and a branched alkyl group comprising from 2 to 8 carbon atoms.

9. The electrolytic solution according to claim 8, A and A' are chosen independently from the phenyl, anthracenyle and naphtalenyle groups, which may be substituted by one or more groups selected from the group consisting of
$—H$,
$—CH_3$,
a halogenide,
a linear alkyl group comprising from 2 to 8 carbon atoms and one or more heteroatoms chosen from O, S, and N, and
a branched alkyl group comprising from 2 to 8 carbon atoms and one or more heteroatoms chosen from O, S and N.

10. The electrolytic solution according to claim 1, having the following general formula:

wherein:
n is an integer in a range of from 1 to 10,
m is equal to 0 or 1,
p is an integer in a range of from 1 to 5,
X— and Y— independently represent a counter-ion of the diazonium cation selected from the group consisting of halogenides, $BF_4—$, $NO_3—$, $HSO_4—$, $PF_6—$, $CH_3COO—$, $N(SO_2CF_3)_2—$, $CF_3SO_3—$, $CH_3SO_3—$, $CF_3COO—$, $(CH_3O)(H)PO_2—$, and $N(CN)_2—$,
$R_1$ and $R_4$ are independently selected from the group consisting of $—CH_2—$, a cyclic alkyl group, an acyclic alkyl group, a linear alkyl group, and a branched alkyl group; and
$R_7$ and $R_8$ are independently selected from the group consisting of $—H$, $—CH_3$, a halogenide, a linear alkyl group optionally having one or more heteroatoms, and a branched alkyl group optionally having one or more heteroatoms.

11. The electrolytic solution according to claim 10, wherein $R_7$ and $R_8$ are independently selected from the group consisting of $—H$, $—CH_3$, a halogenide, a linear alkyl group containing one or more heteroatoms, and a branched alkyl group containing one or more heteroatoms.

12. The electrolytic solution according to claim 10, wherein:

R$_1$ and R$_4$ are independently selected from the group consisting of —CH$_2$—, a cyclic alkyl group, an acyclic alkyl group comprising from 1 to 6 carbon atoms, a linear alkyl group comprising from 1 to 6 carbon atoms, and a branched alkyl group comprising from 1 to 6 carbon atoms; and R$_7$ and R$_8$ are independently selected from the group consisting of —H, —CH$_3$, a halogenide, a linear alkyl group comprising from 2 to 8 carbon atoms, and a branched alkyl group comprising from 2 to 8 carbon atoms.

13. The electrolytic solution according to claim 12, wherein R$_7$ and R$_8$ are independently selected from the group consisting of
- —H,
- —CH3,
- a halogenide,
- a linear alkyl group comprising from 2 to 8 carbon atoms and having one or more heteroatoms chosen from O, S, and N, and
- a branched alkyl group comprising from 2 to 8 carbon atoms and having one or more heteroatoms chosen from O, S and N.

14. The electrolytic solution according to claim 10, having the following general formula:

in which:
n is an integer in a range of from 1 to 10,
m is equal to 0 or 1,
p is an integer in a range of from 1 to 5, X— and Y— independently represent a counter-ion of the diazonium cation chosen from the halogenides, BF$_4$—, NO$_3$—, HSO$_4$—, PF$_6$—, CH$_3$COO—, N(SO$_2$CF$_3$)$_2$—, CF$_3$SO$_3$—, CH$_3$SO$_3$—, CF$_3$COO—, (CH$_3$O)(H)PO$_2$—, and N(CN)$_2$—, R$_1$ and R$_4$ are independently selected from the group consisting of —CH$_2$—, a cyclic alkyl group, an acyclic alkyl group, a linear alkyl group, and a branched alkyl group; and R$_7$ and R$_8$ are independently selected from the group consisting of —H, —CH$_3$, a halogenide, a linear alkyl group optionally having one or more heteroatoms, and a branched alkyl group optionally having one or more heteroatoms.

15. The electrolytic solution according to claim 14, wherein R$_7$ and R$_8$ are independently selected from the group consisting of —H, —CH$_3$, a halogenide, a linear alkyl group comprising one or more heteroatoms, and a branched alkyl group comprising one or more heteroatoms.

16. The electrolytic solution according to claim 14, wherein:

R$_1$ and R$_4$ are independently selected from the group consisting of —CH$_2$—, a cyclic alkyl group, an acyclic alkyl group comprising from 1 to 6 carbon atoms, a linear alkyl group comprising from 1 to 6 carbon atoms, and a branched alkyl group comprising from 1 to 6 carbon atoms; and R$_7$ and R$_8$ are independently selected from the group consisting of —H, —CH$_3$, a halogenide, a linear alkyl group comprising from 2 to 8 carbon atoms, and a branched alkyl group comprising from 2 to 8 carbon atoms.

17. The diazonium salt according to claim 16, wherein R$_7$ and R$_8$ are independently selected from the group consisting of
- —H,
- —CH$_3$,
- a halogenide,
- a linear alkyl group comprising 2 to 8 carbon atoms and one or more heteroatoms chosen from O, S, and N, and
- a branched alkyl group comprising from 2 to 8 carbon atoms and one or more heteroatoms chosen from O, S, and N.

18. The electrolytic solution according to claim 10, wherein R$_7$ and R$_8$ are identical and represent —H.

* * * * *